US012734313B2

(12) United States Patent
Gjertsen et al.

(10) Patent No.: US 12,734,313 B2
(45) Date of Patent: Sep. 15, 2026

(54) HAND OPERATED DEVICES FOR ADMINISTRATION OF A MEDICAMENT

(71) Applicant: ZETEO Biomedical, LLC, Austin, TX (US)

(72) Inventors: Jeff Gjertsen, Cedar Park, TX (US); Timothy Sullivan, Austin, TX (US)

(73) Assignee: Zeteo Biomedical, LLC, Austin, TX (US)

( * ) Notice: Subject to any disclaimer, the term of this patent is extended or adjusted under 35 U.S.C. 154(b) by 880 days.

(21) Appl. No.: 17/436,236

(22) PCT Filed: Mar. 26, 2020

(86) PCT No.: PCT/US2020/025076
§ 371 (c)(1),
(2) Date: Sep. 3, 2021

(87) PCT Pub. No.: WO2020/198536
PCT Pub. Date: Oct. 1, 2020

(65) Prior Publication Data

US 2022/0152319 A1 May 19, 2022

Related U.S. Application Data

(60) Provisional application No. 62/824,788, filed on Mar. 27, 2019, provisional application No. 62/948,777, filed on Dec. 16, 2019.

(51) Int. Cl.
*A61M 11/00* (2006.01)

(52) U.S. Cl.
CPC .................................. *A61M 11/007* (2014.02)

(58) Field of Classification Search
CPC ................ A61M 11/007; A61M 11/06; A61M 15/0036; A61M 15/0031; A61M 15/0028; A61M 15/08; A61M 2205/071; A61M 35/003
See application file for complete search history.

(56) References Cited

U.S. PATENT DOCUMENTS 6,708,846 B1 3/2004 Fuchs et al.
6,725,857 B2 * 4/2004 Ritsche ............. A61M 15/0045 128/200.14
7,726,519 B2 6/2010 Heldt et al.
8,377,009 B2 2/2013 Sullivan et al.
2002/0032409 A1 3/2002 Ritsche
(Continued)

FOREIGN PATENT DOCUMENTS

DE 19905993 A1 8/2020
DE 20121064 A1 3/2021
EP 1084763 A2 3/2021

OTHER PUBLICATIONS

International Search Report and Written Opinion issued in relation to International Application No. PCT/2020/025076.
(Continued)

*Primary Examiner* — Bhisma Mehta
*Assistant Examiner* — Fatimata Sahra Diop

(57) ABSTRACT

A handheld assembly for dispensing a medicament to a subject is provided. The assembly includes a unit dose device, a shell, a plunger, a dispense button, a drive member and an escapement that is movable and capable of cycling the dispense assembly thru multiple states of a dispense cycle.

9 Claims, 12 Drawing Sheets

(56) References Cited

U.S. PATENT DOCUMENTS

| | | | |
|---|---|---|---|
| 2006/0243275 A1 | 11/2006 | Ruckdeschel | |
| 2007/0131717 A1 | 6/2007 | Davies et al. | |
| 2008/0210228 A1 | 9/2008 | Corbacho | |
| 2010/0331765 A1 | 12/2010 | Sullivan et al. | |
| 2013/0158474 A1* | 6/2013 | Sullivan | A61M 11/06 604/68 |

OTHER PUBLICATIONS

European Supplementary Search Report issued Nov. 16, 2022 in relation to EP Application No. EP20778981.

* cited by examiner 232
235
120
110
230
220

232
120
235
110
230
220

130
232
120
235
110
230
220

232
120
110
230
220

232
230
220

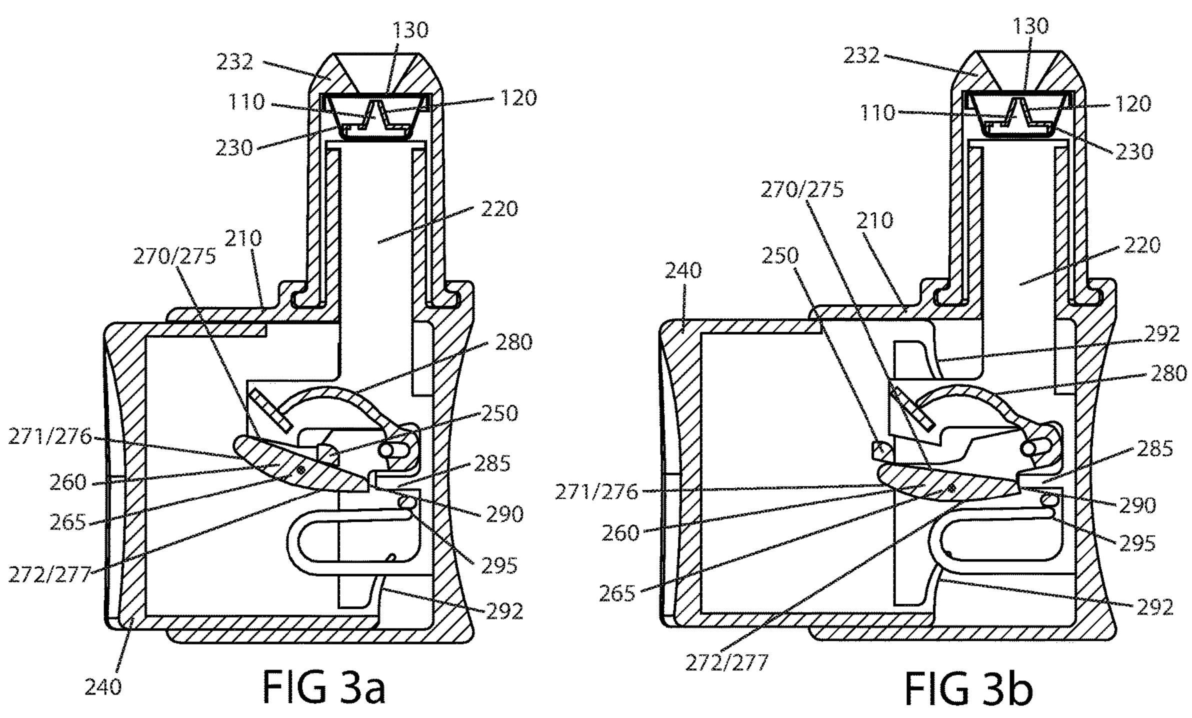
FIG 3a
FIG 3b
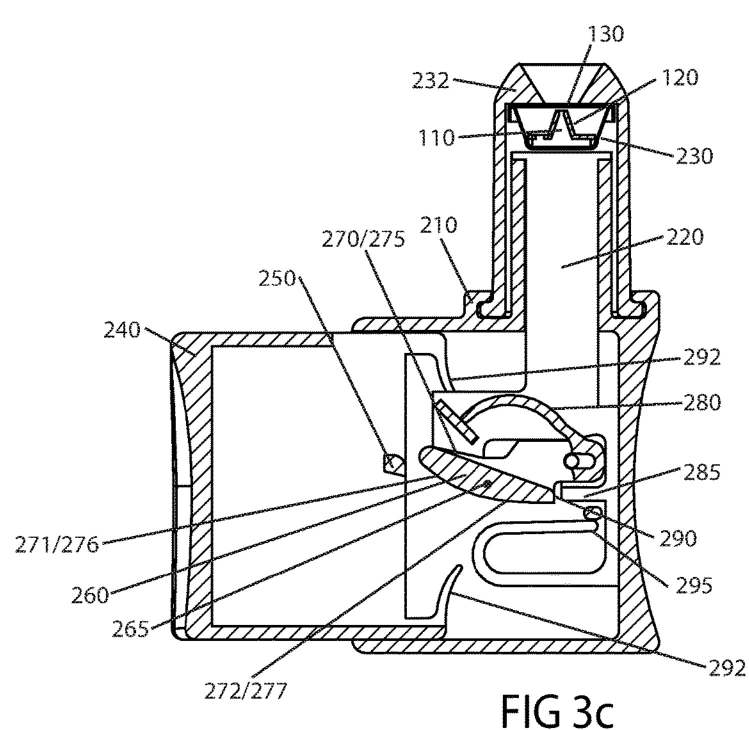
FIG 3c 130
232
110
120
230
220
210
270/275
280
250
271/276
265
285
260
290
272/277
295
292
240

130
232
110
120
230
270/275
210
220
250
240
292
280
265
285
271/276
290
260
295
292
272/277

HAND OPERATED DEVICES FOR ADMINISTRATION OF A MEDICAMENT

CROSS REFERENCE TO RELATED APPLICATIONS

This application is a national stage application filed 35 U.S.C. § 371 from PCT Application PCT/US20/25076 entitled "Hand Operated Devices for Administration of a Medicament" filed on Mar. 26, 2020, which claims priority and benefit of U.S. Provisional Patent Applications 62/824,788 and 62/948,777 filed on Mar. 27, 2019 and Dec. 16, 2019 respectively; both entitled "Cycling Plunger Device and Method for Administration of a Medicament." The content of these applications is hereby incorporated in their entirety by reference.

BACKGROUND OF THE INVENTION

Technical Field

Embodiments of the subject matter disclosed herein generally relate to medical devices and systems for administering medicaments to a subject; more particularly, hand operated devices and systems for dispensing a unit dose form containing a medicament to a subject.

Discussion of the Background

Certain diseases and medical conditions that are systemic, neurological or local are treatable via the administration of drugs and therapeutic agents taken topically or systemically through the eye, ear, mouth, nose, lungs or dermal skin layer. A number of pharmaceutical or biologic agents are deliverable as liquids, suspensions, emulsions, powders or particles orally to the lungs, sublingual, buccal or intra-nasally (including nose to brain), and may be administered for topical, systemic or intracranial deposition, including but not limited to antibiotics, antipyretics, anti-inflammatories, beta-blockers, biologics, biosimilars, cannabinoids, vitamins, botanicals, co-factors, enzymes, inhibitors, activators, nutrients, vaccines including DNA based killed or live virus or microorganisms, nucleic acids, proteins, peptides, antibodies, peptide mimetics, prophylactic or therapeutic immune-modulators, anti-viral and anti-bacterial compounds, biologics, diagnostic agents and other agents, pharmaceutical compositions or medicaments.

Hand operated devices (either as single use or multi-use devices) have been developed to deliver dose quantities where each expression by hand of the device delivers an individual dose. For example, Fuchs et al. U.S. Pat. No. 6,708,846 teaches a reusable dispenser unit and a media container for a medicament for intranasal administration. The device has a release button and a compressed spring that pushes against a rod and discharges the drug. Ritsche et al. U.S. Pat. No. 6,725,857 claims a multi-dose strip of blisters sequentially expressed by a device with a spring-loaded firing button attached to a pretensioned storage element that rotates a conveying drum. Sullivan et al. U.S. Pat. No. 8,377,009 discloses handheld devices with a sliding mechanism and an angled cam attached to a firing button which activates a plunger for discharging a crushable unit dose ampule or blister.

SUMMARY OF EXAMPLE EMBODIMENTS

According to an embodiment, there is a handheld assembly for dispensing a medicament to a subject. The assembly includes a unit dose form containing a medicament; a shell; a plunger; a dispense button; a drive member in communication with the dispense button; and a plunger escapement having more than one ramp wherein each ramp has a predetermined profile. A first motion of the dispense button causes the drive member to translate along a first ramp of the plunger escapement member readying the assembly for dispense, a second motion of the dispense button causes the drive member to translate along a second ramp of the plunger escapement member extending the plunger to express the unit dose form.

According to another embodiment, there is a handheld assembly for dispensing a medicament to a subject. The assembly includes a shell; a dispense button; a plunger; a single plunger escapement member with a plurality of ramp surfaces; and a drive member disposed on the dispense button. A first motion of the dispense button causes the drive member to translate along a plunger escapement member ramp surface and a second motion causes the drive member to translate along a second plunger escapement member ramp surface to cycle the dispense button and the plunger between plural dispense states.

According to yet another embodiment, there is a handheld assembly for dispensing a medicament to a subject. The assembly includes a shell with more than one exterior surface and housing a dispense button, a plunger, and an escapement having more than one ramp surface; a hollow cylindrically shaped dispense tip body having an outer surface, a domed distal end having a thru hole, a unit dose form containing a medicament positioned within the distal end, and a base end having at least one tab member. A shell surface has one or more splines configured to rotatably interlock with the tabs of the dispense tip to removably affix the dispense tip to the shell.

BRIEF DESCRIPTION OF THE DRAWINGS

The accompanying drawings, which are incorporated in and constitute a part of the specification, illustrate one or more embodiments and, together with the description, explain these embodiments. In the drawings:

FIGS. 3A thru 3C show an exemplary handheld assembly during the make ready stage.

DETAILED DESCRIPTION OF EXAMPLES OF THE INVENTION

Figures 1A, 1B, 1C, 1D, 1E:
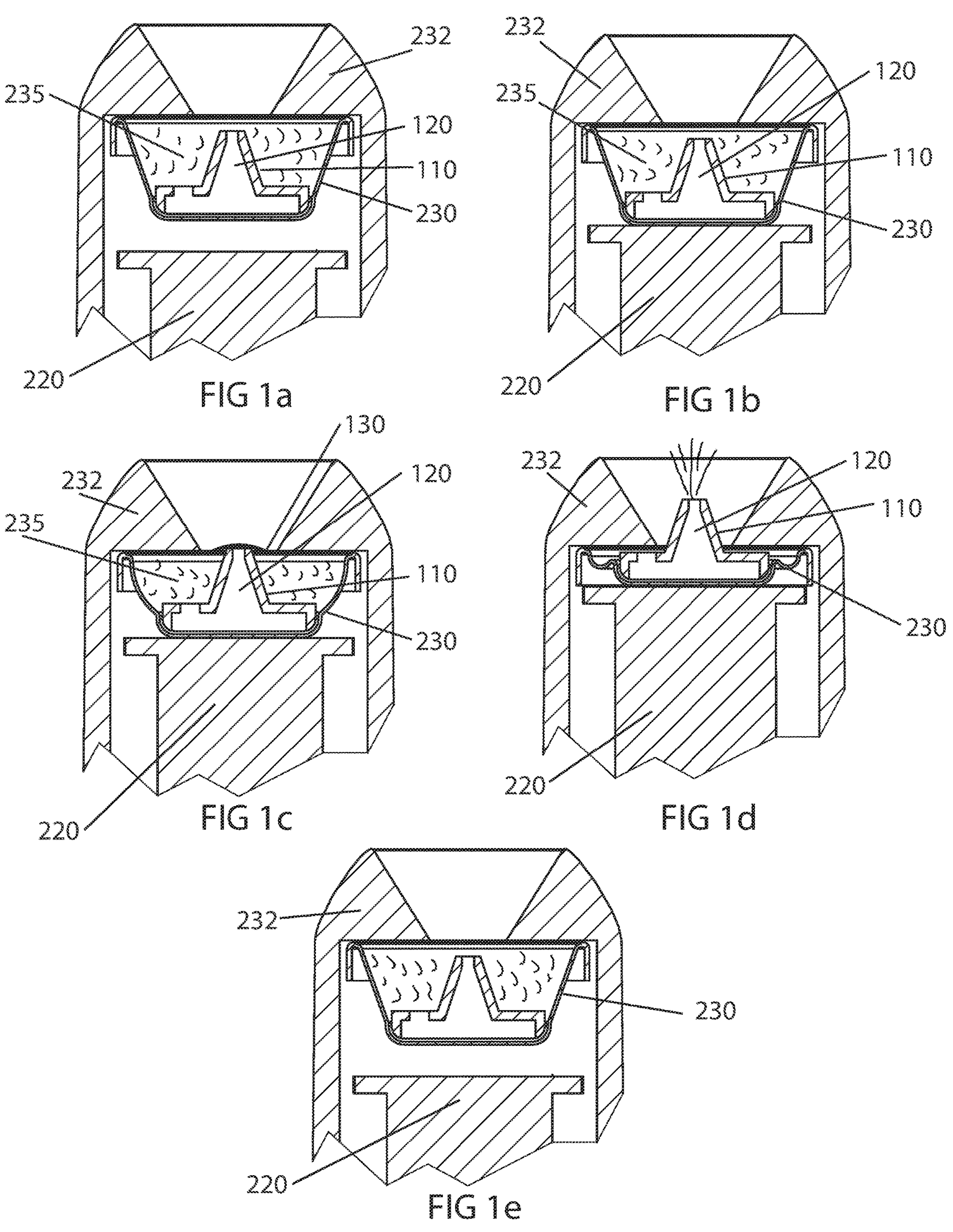
FIGS. 1A thru 1E illustrate an exemplary set of stages of dispense.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to devices and systems for precisely controlled dose delivery of a medicament to a subject. However, the embodiments discussed herein are not limited to such elements.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the described features, structures or characteristics may be combined in any suitable manner in one or more embodiments.

The following is a limited list of examples of general classes of medicaments administered through the nasal or oral cavity or topically to the eye, ear or skin as liquids, solutions, suspensions, emulsions, powders or reconstituted powders for a host of indications which can include but not limited to anemia, asthma, bronchitis, rhinitis, flu, cancer, cystic fibrosis, diabetes, inflammation, osteoporosis, hepatitis, arthritis, chronic or acute pain, immunodeficiency disorders, multiple sclerosis, endocrinological disorders, neurodegenerative disorders, ocular disorders, metabolic disorders, man-made or naturally occurring bioterror threats, dermal disorders and wounds, etc. Drug compounds for treating those indications include various adjuvants, calcitonin, erythropoietin, heparin, inhibitors, insulin, interferons, interleukins, hormones, neurotropic agents, growth factors, stimulating factors, vasodilators and constrictors, antibiotics, antipyretics, anti-inflammatories, biologics, probiotics, vitamins, co-factors, enzymes, inhibitors, activators, nutrients, aptamers, thioaptamers, anti-virals, immunomodulators, diagnostic agents, vaccines including killed or live virus or microorganisms, nucleic acids, proteins, peptides, antibodies, peptide mimetics, micro or nanoparticles. This list is not intended to be exhaustive and in no way is inclusive of all possible conditions and diseases, drugs and compounds, or routes or targets of administration, but rather is to illustrate the breadth of medicaments and other agents and indications employable in the present invention and contemplated by the present disclosure. For simplicity, the various agents dispensable by devices and system of the present disclosure will herein be referred to as medicaments which is intended to encompass pharmaceutical and non-pharmaceutical agents.

Blister-based unit dose forms provide a safe, convenient, sterile, easily stored and transported, and controlled dose platform to deliver those medicaments to a subject via a target route of administration. The devices and assemblies that express the unit dose forms can provide for simplified self-administration by a user or may be administered by a medical professional to a subject. A subject may be a human or non-human animal.

However, as explained in detail below, the unit dose forms require a simple but precise device in order to provide an accurate, full, efficient (low waste), and repeatable dose to a subject. Thus, it is desirable that the dispensing device perform precisely through each stage of the dose dispense sequence. Moreover, the device should preferably be operable by hand, include single as well as reusable embodiments and thus be capable of delivering sequential precise doses to a subject.

The unit dose forms of the present disclosure, in preferred embodiments, are crushable blisters. Note herein that said dosage forms are commonly referred to in the art using alternative terms as forms, units, unit dose or unit dosage forms, blisters, blister packs, blister wells, wells, chambered wells, ampoules, primary containers, or similar terminology. The dosage forms described herein generally as "unit dose", "unit dose forms", "wells", "blisters" or "chambered wells", etc. are used interchangeably and are intended to encompass the full scope of known formed receptacles commonly in use for medicament substance storage and delivery.

The manufacturing processes for forming unit dose forms in a continuous web can include a step of drawing a metal, polymer, or laminated metal-polymer foil or other suitable sheet of material with the appropriate mechanical characteristics to allow hot, warm or cold forming and drawing are known in the art and contemplated herein. In certain embodiments, one or more forming pins can be used to form a primary contour, the contour having a depth of at least 100% and up to 150% of the depth of the final formed recess or well. A second stage involves shaping the primary contour with one or more of the same or additional forming pin(s) to the desired formed recess depth and shape, with a depth that is less than the depth of the primary contour, while substantially maintaining the surface area of the primary contour formed in the first stage. The contour or shape of the blister well can be formed to contain certain shape features, indentations, or be imparted with texture by the forming pins to provide for a means of securing the internal piercing device within the blister well or recess.

The formed well or recess is then typically loaded aseptically with the predetermined quantity of medicament or other material for administration to a subject and in certain preferred embodiments disclosed herein, an internal piercing device is placed into the formed well. A lidding material (or "lidstock') of the same or similar laminated material as the blister well or other sheeting material is then rolled atop the well and bonded to the well sheeting with adhesives, or by pressure, thermal, ultrasonic or other welding means.

In certain embodiments, the individual dose forms that can be formed in sheets which are in later manufacturing steps, singulated into individual doses for use in single-use, disposable, non-reloadable devices, or for use in devices which are reloadable with additional unit doses for subsequent dosing of the same or different subject(s). Alternatively, and depending upon the application and indication, the sheets may be formed and cut into rows, arrays, grids or other configurations of blisters suitable for use in multi-dose devices or cartridges to be used in such devices. Numerous commercially available laminated structures can be manufactured using known materials and methods which facilitate the production of variable strength of seal between opposing faces, are known in the art and are readily contemplated by the present disclosure.

Regardless of the shape, size, or geometric configuration of the unit dose form; in certain embodiments each unit dose contains an internal piercing device member. The internal piercing member can be manufactured by techniques known by those skilled in the art, for example injection molding or machining. The piercing member can be constructed of any material with suitable chemical compatibility and mechanical properties to impart the design strength characteristics examples include ceramic, glass, metal, composites, polymeric plastics etc. In preferred embodiments the internal piercing member may be constructed from polymeric materials to include but not limited to polyethylene (PET), polypropylene, polyetherimide (PEI), polysulfone (PSU), polyaryletherketone (PAEK), polystyrene, or poly ether ether ketone (PEEK), self-reinforced polyphenylene (SRP) or other pharmaceutical or medical grade material or materials.

In preferred embodiments, the internal piercing members are typically injection molded as single piece components, however in certain other embodiments where particular structural features (to be described in greater detail below) are less amenable to one-piece molding; the piercing members can be assembled from multiple machined, printed and/or molded parts. For example, certain embodiments may entail attaching by press fit, friction fit, snap fit, or threading a machined metal or separately molded elongated tip to a plastic base part. Other combinations of parts, manufacturing methods, materials, and assembly methods are known in art and fully contemplated herein. In preferred embodiments, the elongated tip of the piercing member may contain at least one internal channel which provides a high velocity liquid stream and serves as a nozzle for dispensing a medicament as a liquid spray or dispersed powder. According to other embodiments, the elongated tip may be solid (i.e. no internal channel), but the surface may include striations, ribs, spirals or the like to aid in dispersion of a powder once the elongated tip pierces the lidstock.

An overview of a set of stages for the dispensation of a medicament utilizing a handheld assembly with a plunger and other components acting upon a unit dose form are shown in FIGS. 1A-E. The initial stage as shown in FIG. 1A is typically characterized as the "ready to load" stage, whereby a plunger 220 is first positioned to accept a dispense tip 232 preloaded with a unit dose form 230 containing a medicament 235. The unit dose forms as shown contain an internal piercing member 110 which in preferred embodiments itself includes an internal channel 120 for passage of the medicament 235. Once the unit dose is loaded and the plunger 220 is in contact with the unit dose 230 as shown in FIG. 1B the device is prepared for activation, which may be referred to as "ready to dispense", or "make ready" stage or state.

In the "activation" or "dispense" stage, the plunger is acted upon by other device components, the sequence of which will be described in detail below. Plunger 220 further extends and begins to pressurize the unit dose form 230 as shown in FIG. 1C. In this next stage, as the unit dose form 230 begins to breach the unit dose form's lidding material 130 until it punctures and the internal channel 120 of the internal piercing member 110 is now in communication with the exterior. Once punctured, the pressurized medicament 235 within the unit dose enters the internal piercing member 110 internal channel 120. The stage shown in FIG. 1D is where the unit dose form 230 is crushed and medicament 235 exits the unit dose and is dispensed to a subject via the desired route of administration.

Finally, once the medicament is dispensed to a subject, the assembly in certain embodiments may be undergo one or more steps in order to be returned to its original state ready for another dispense. This stage will be referred to as the "return" stage and is shown in FIG. 1E.

There are several key dispense characteristics impacted by the design of the device components, particularly the plunger action which generates the internal pressurization and expression of the contents out of the unit dose form. Those performance characteristics include, for example, the dispense efficiency, defined as the fraction of the dose actually dispensed; the characteristics of the dispense spray (droplet size, droplet distribution, spray pattern, plume geometry etc.); the degree of cross contamination between unit dose forms occurring as a result of holdover medicament remaining within or upon the unit dose form following dispense; as well as the convenience and ease of a user's experience with the device, among other aspects.

Figure 2:
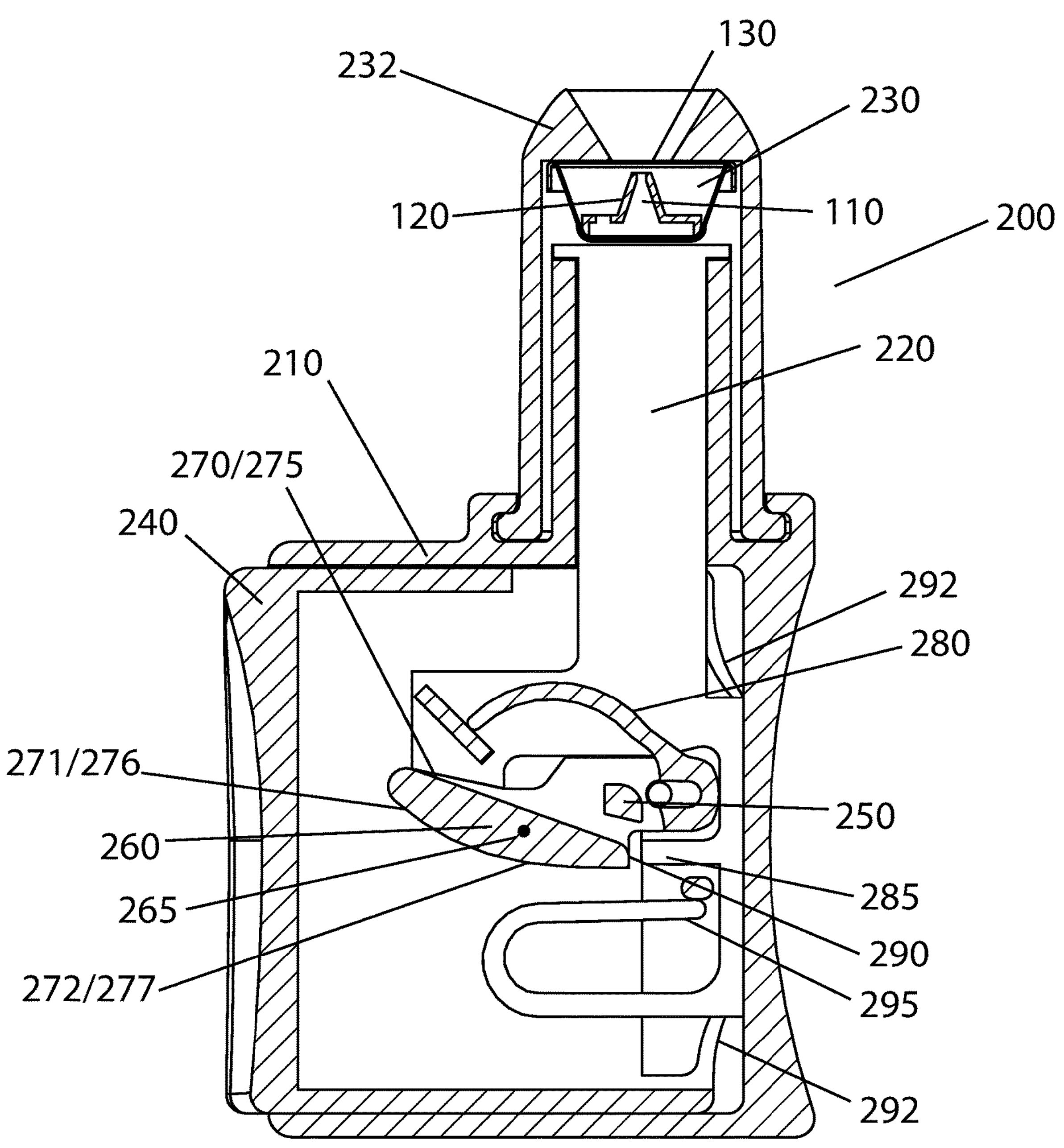
FIG. 2 shows an exemplary handheld assembly in its initial stage.

An exemplary handheld assembly for administering a medicament to a subject is shown in FIG. 2. The assembly 200 comprises a shell 210 for housing components of the handheld assembly. Shell 210 may be comprised of two halves (one half is shown) which are injected molded and snap fitted together, for example. A plunger 220 is at least partially enclosed within shell 210 and extends from the shell and configured to express the unit dose form 230 containing a medicament 235. In preferred embodiments, unit dose form 230 is contained within a dispense tip 232 that is configured to attach to the shell 210. Also, in preferred embodiments, unit dose form 230 also contains an internal piercing member 110 which itself includes an internal channel 120.

A dispense button 240 is at least partially enclosed within shell 210 and extends from the shell and is slidable between the shell halves when acted upon by a user's hand. A drive member 250 is located within shell 210 and is in communication with dispense button 240 and in preferred embodiments drive member 250 is comprised of a post or other protrusion attached to or molded as part of dispense button 240.

A plunger escapement member 260 (hereinafter "escapement") is also contained within shell 210 and is movable (rotatable and/or translatable) about an axis 265 within shell 210. Escapement 260 may be a polygonal body having multiple sides which comprise at least one ramp 270 upon its surface (four ramps 270, 271, 272 and 290 are shown in this example). The escapement 260 may be a solid or hollow molded or machined body. In the context of the present disclosure, an escapement shall refer to device or body that provides mechanical linkage between at least one source body to at least one other receiver body. Such devices are used to provide a step wise mechanical action when acted upon by an energy source. Each ramp 270 upon its surface has a predetermined profile 275 comprised of a radius of curvature, a linear slope or combination of the two in one or more sections upon the surface. Each ramp 270 is configured to provide a defined action when drive member 250 translates along its surface, to be described below in greater detail.

Assembly 200 may also include a plunger escapement member return spring 280; a plunger hold surface 285; a reset ramp surface 290; a dispense button return spring 292 at the base dispense button 240, and a plunger return spring 295 all of which are to be described in detail below.

The assembly as shown in FIG. 2 is in its initial stage characterized as "ready to load" meaning plunger 220 is in a retracted and able to accept dispense tip 232 with unit dose 230. Dispense button 240 is also in a retracted state meaning it is substantially withdrawn within shell 210. Escapement 260 is in its initial static position as well.

In the "make ready" stage as shown in FIGS. 3A-C, dispense button 240 is extended, i.e. withdrawn from shell

210 which causes drive member 250 to make contact with (FIG. 3A) and then translate along a first ramp 270 on the upper surface of escapement 260. In an exemplary embodiment, first ramp's 270 predetermined profile 275 is a single section with a constant slope, though other profiles may be contemplated. For example, as shown in the figures, second ramp 271, though comprising a single side or face of escapement 260, has two ramp sections (271 and 272) of varying profile (276 and 277, respectively) whereby a first section 271 has an initial curvature or radius, followed by a second section 272 of a substantially flat or linear slope.

As escapement 260 is acted upon by translating drive member 250, it (escapement 260) rotates around an axis 265 (not shown behind escapement body), moving it out of the way of the drive member 250. FIG. 3B shows dispense button 240 extended and drive member 250 at left edge of escapement 260. Once dispense button 240 is fully extended and drive member 250 is clear of escapement 260, as shown in FIG. 3C, escapement spring 295 will move the escapement 260 back to its position, thus placing the assembly in a make ready state.

Figures 4A, 4B:
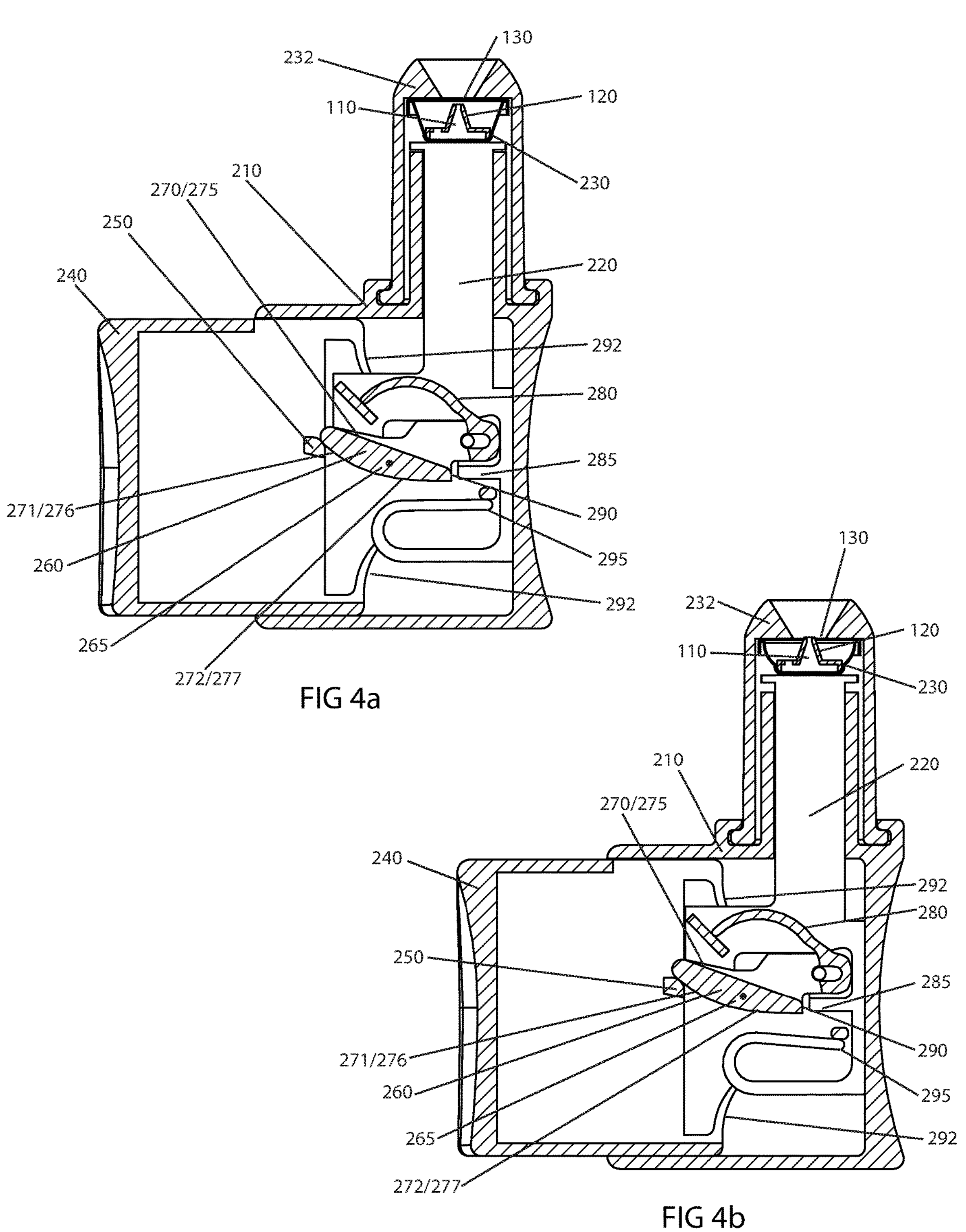
FIGS. 4A and B show an exemplary handheld assembly during early dispense stage.

At the beginning of the dispense activation stage, as shown in exemplary FIG. 4A, dispense button 240 is depressed into shell 210 which causes drive member 250 to travel back towards escapement 260 until it engages with a second ramp 271 on the escapement's underside (in this embodiment) with a separate predetermined profile 276. As dispense button 240 is continued to be depressed, as shown in FIG. 4B, drive member 250 translates along second ramp 271 which causes escapement 260 to make contact with and extending plunger 220 compressing unit dose 230.

Figure 5:
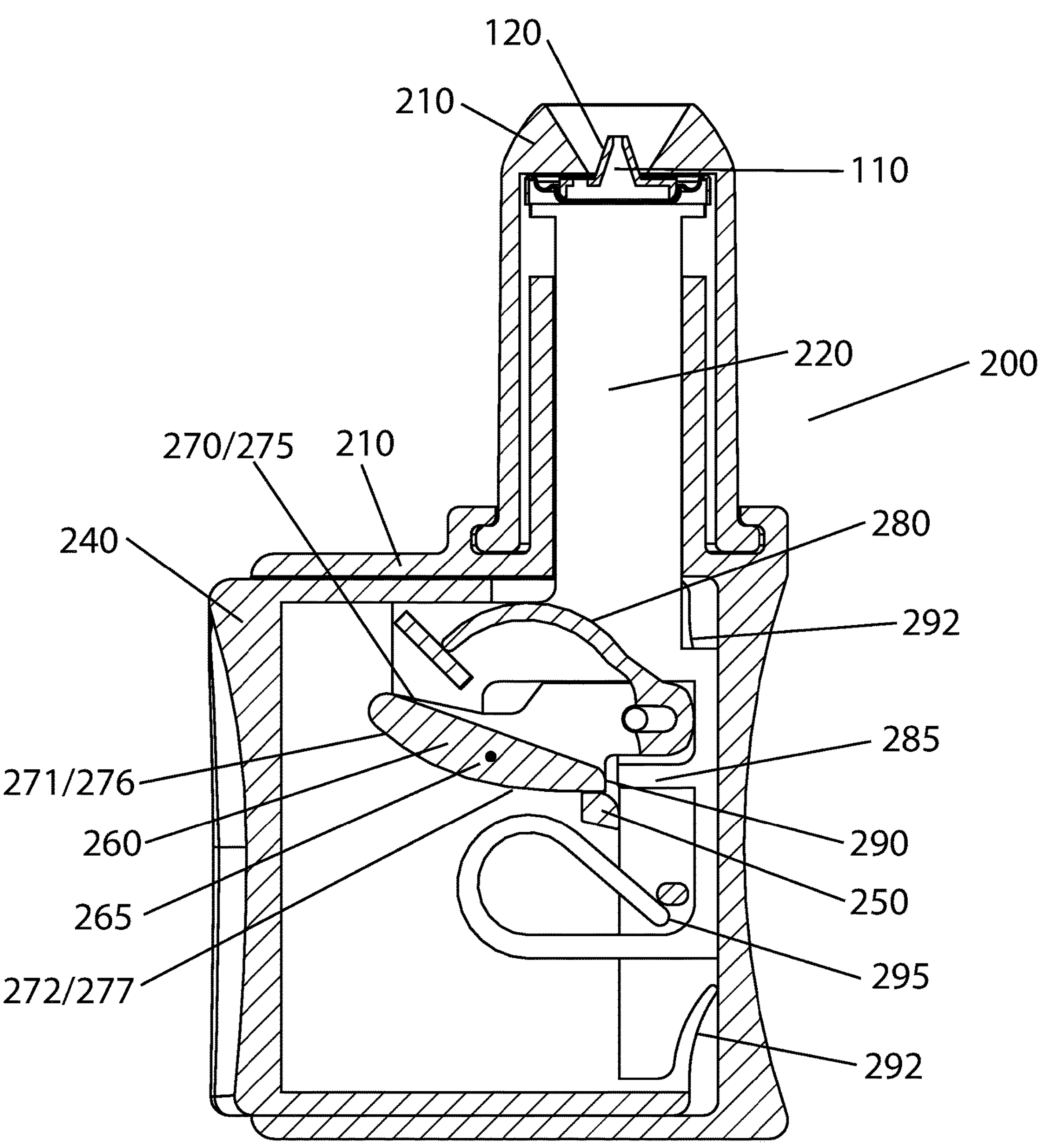
FIG. 5 shows an exemplary handheld assembly drive member translating along a second ramp during dispense.
Figure 6:
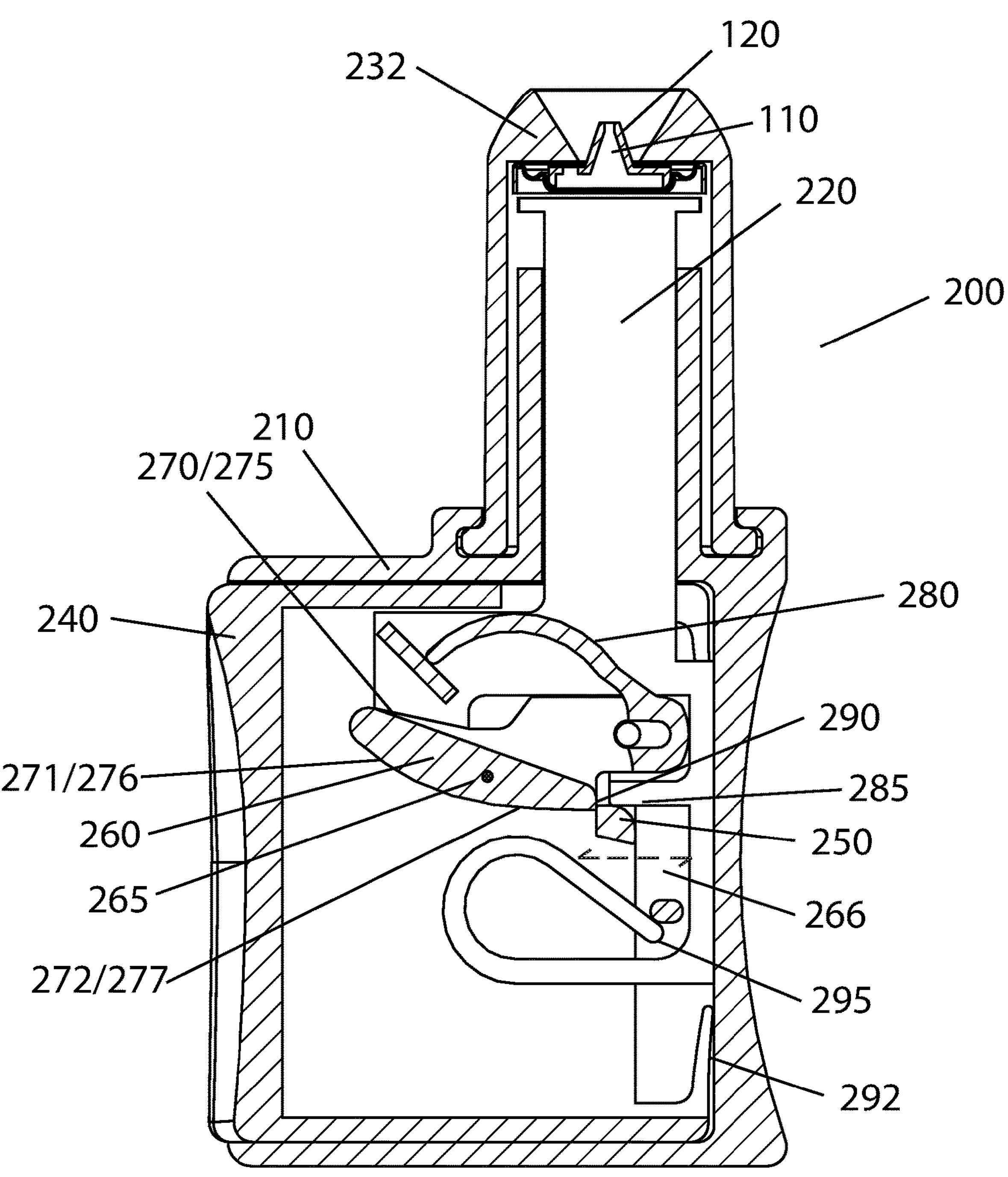
FIG. 6 shows an exemplary handheld assembly drive member engaging a plunger hold surface during dispense.

As shown in FIG. 5, drive member 250 continues to translate along the second ramp 271 during the dispense activation until it reaches the end of the second ramp while plunger 220 continues to compress unit dose 230 and dispensing medicament 235. Prior to drive member 250 reaching the end of second ramp 270, plunger return spring 295 engages with shell 210. Optionally, when drive member 250 reaches the end of second ramp 270, drive member 250 engages with plunger hold surface 285 near the base of plunger 220 as shown in FIG. 6. Plunger hold surface 285 serves as stopping point in the dispense which allows drive member 250 to hold the plunger in an extended position until dispense button 240 is released.

Figure 7:
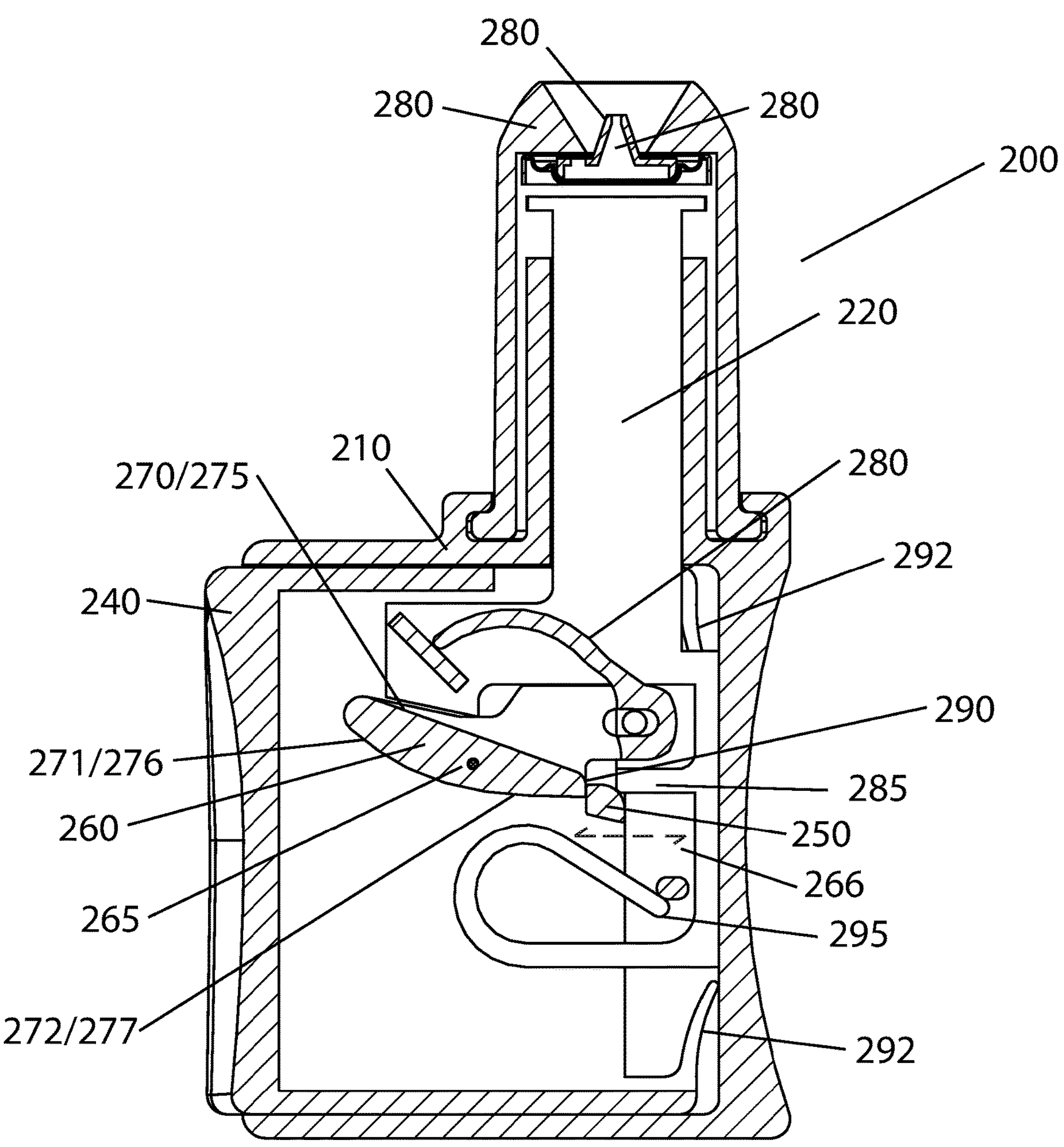
FIG. 7 shows an exemplary handheld assembly drive member engaging a reset surface during dispense.

In certain preferred embodiments, at the end of the dispense stage, dispense button 240 is released by the user, and one or more dispense button return springs 292 will push dispense button 240 outward from shell 210 causing drive member 250 to press out on reset surface 290 located on the end of escapement 260 as shown in FIG. 7. In this embodiment, the reset surface 290 comprises a fourth ramp on escapement 260, which acts as turning point for drive member 250 to reverse direction. In this embodiment, escapement 260 may move in a translational motion along axis 266 (depicted by arrows) in a vertical direction when acted upon by plunger return spring 295.

Figure 8:
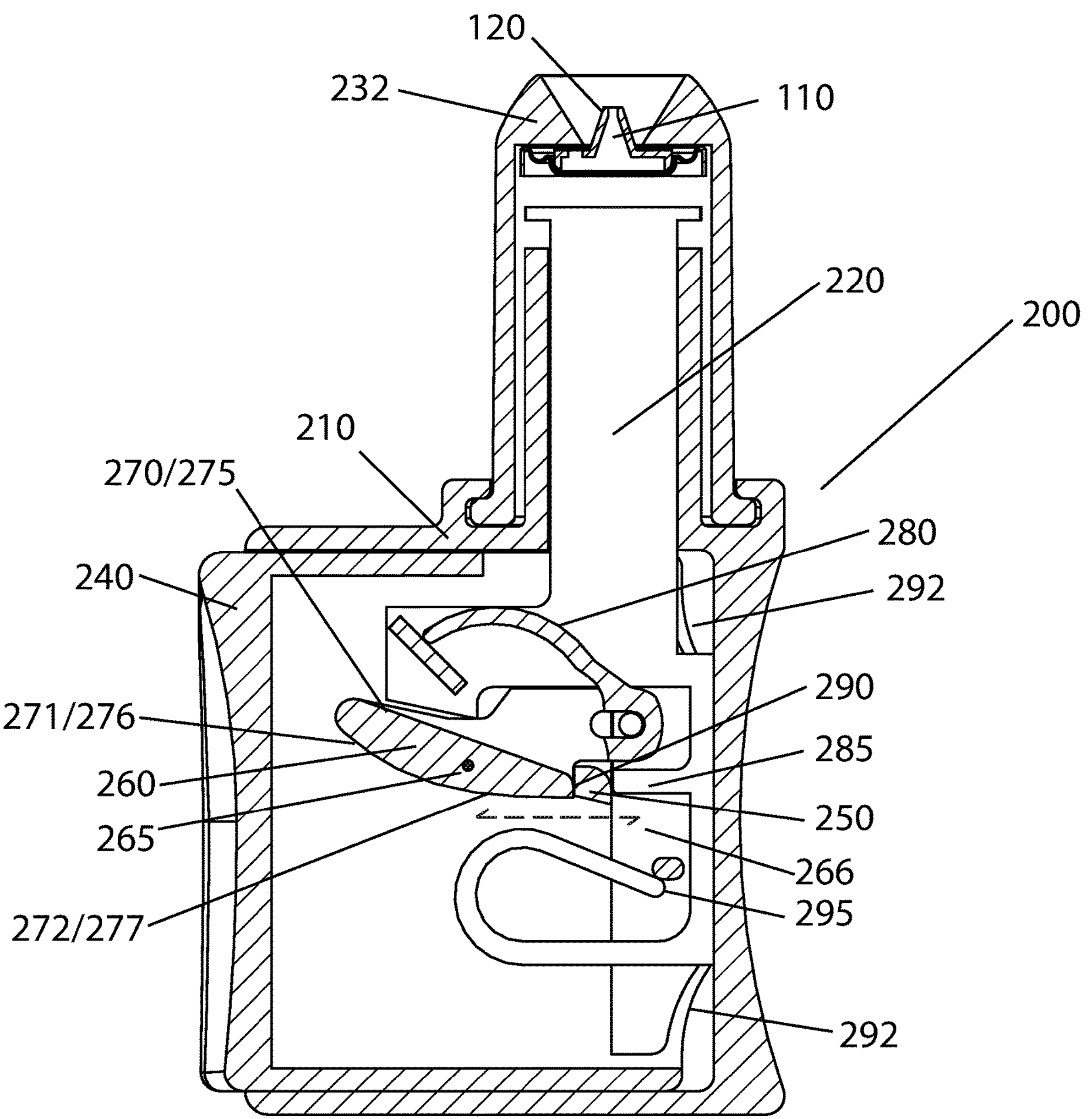
FIG. 8 shows an exemplary handheld assembly drive member passing in between the escapement and plunger hold surface during dispense.
Figure 9:
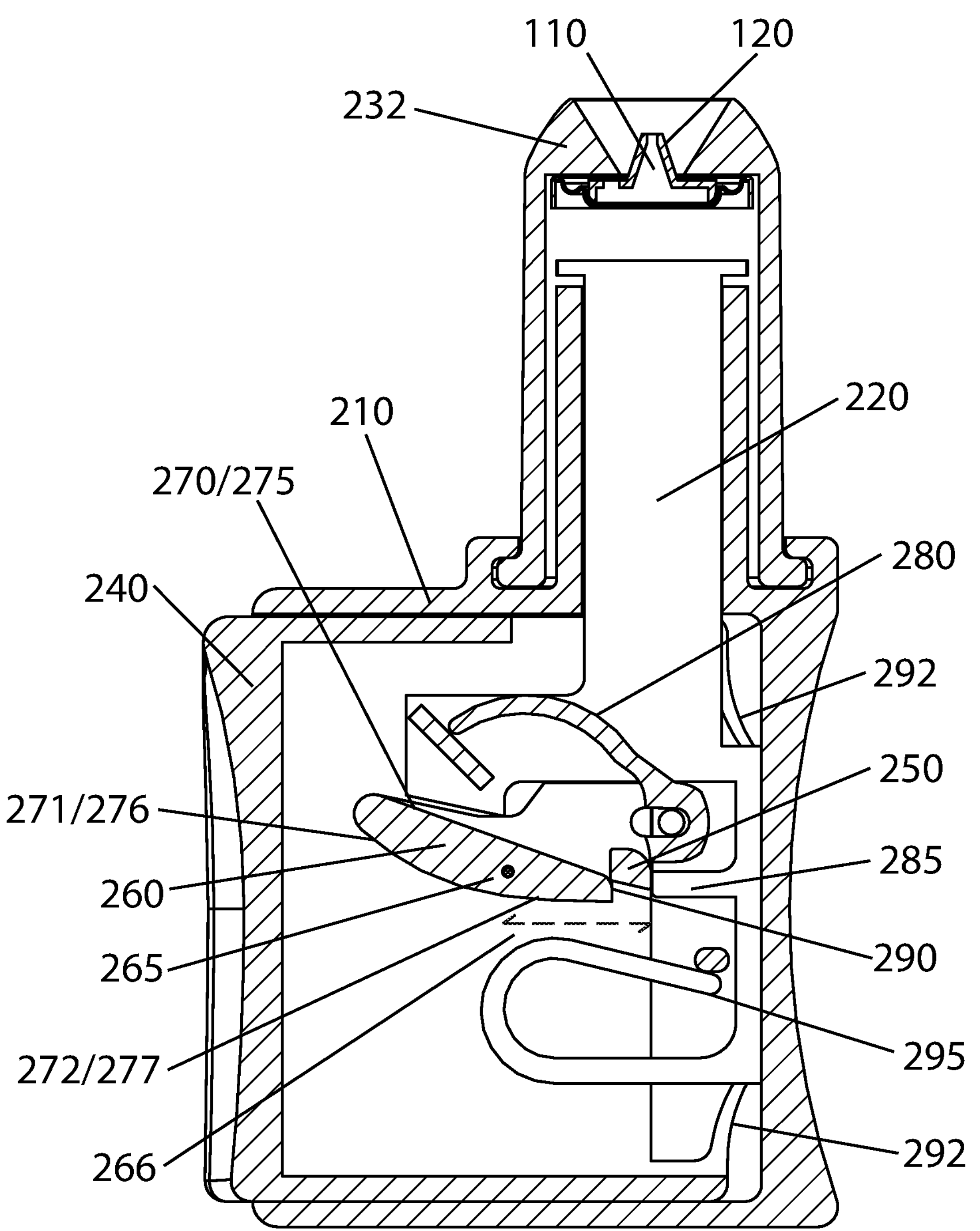
FIG. 9 shows an exemplary handheld assembly with its mechanisms returned to their original state following dispense.

Escapement 260 will move along this second axis 266 until there is enough space between the second ramp 270 on the escapement and the plunger hold surface 285 for drive member 250 to pass between the two bodies as shown in FIG. 8. When this occurs, plunger 220, driven by plunger return spring 295, will retract back to its static position and escapement 260 will return to initial state (i.e. "return" stage) position once reset surface 290 has been cleared. At this point the dispenser assembly 200 has returned with all of the mechanisms in their original state prepared for a subsequent cycle of dispense (FIG. 9).

As shown in the figures, plunger return spring 295 may be comprised of a partial loop attached to a surface within inner shell 210 body, and in other embodiments it may be attached to dispense button 240. It may be molded as a single part or attached or welded as a separate part and may be comprised of the same or different material.

Similarly, as shown for example in FIG. 7, the dispense button return spring 292 may be provided as a feature molded together with the dispense button 240 and typically comprised of a curved surface capable of bending and thus storing energy as a spring.

Also as shown, for example, in FIG. 5, certain embodiments of the assembly may include a plunger escapement return spring 280. At the end of the dispense, once dispense button 240 is released, this spring acts to pull back or reverse plunger 220. This action is beneficial for avoiding or reducing cross contamination among unit dose forms, particularly between those dispensed and those awaiting dispense in a multi-dose embodiment. A dispensed unit dose form has a tendency for surface tension and other charge effects to cause a droplet of the medicament material to remain at the tip; typically partially within and outside the internal channel 120 of the internal piercing member 110 once it has punctured the unit dose 230 lidstock. As discussed earlier, the unit dose form 230 is typically comprised of metal and polymer laminates which while crushable, retain some elasticity under deformation. When spring 280 draws back plunger 220 following dispense, the unit dose form 230 elastically expands, drawing inward the adhering droplet of medicament where it largely remains, dries and is thus unable to transfer to other unit doses or other surfaces of the dispense assembly.

Other embodiments are readily contemplated by the disclosure herein. For example, assembly 200 may be configured for single use whereby escapement 260 is comprised of a single ramp 270 for dispense or include two ramps one for "make ready" (270) and one for dispense (271). In this embodiment, dispense button 240 may originate in extended form and thus already configured ready to dispense, or non-extended and thus for compactness retractable for "make ready" staging prior to dispense. In both these single-use embodiments, the dispense button following dispense may be pressable back into the housing following dispense, again for compactness, without cycling the device components for another dose.

Figures 10A, 10B:
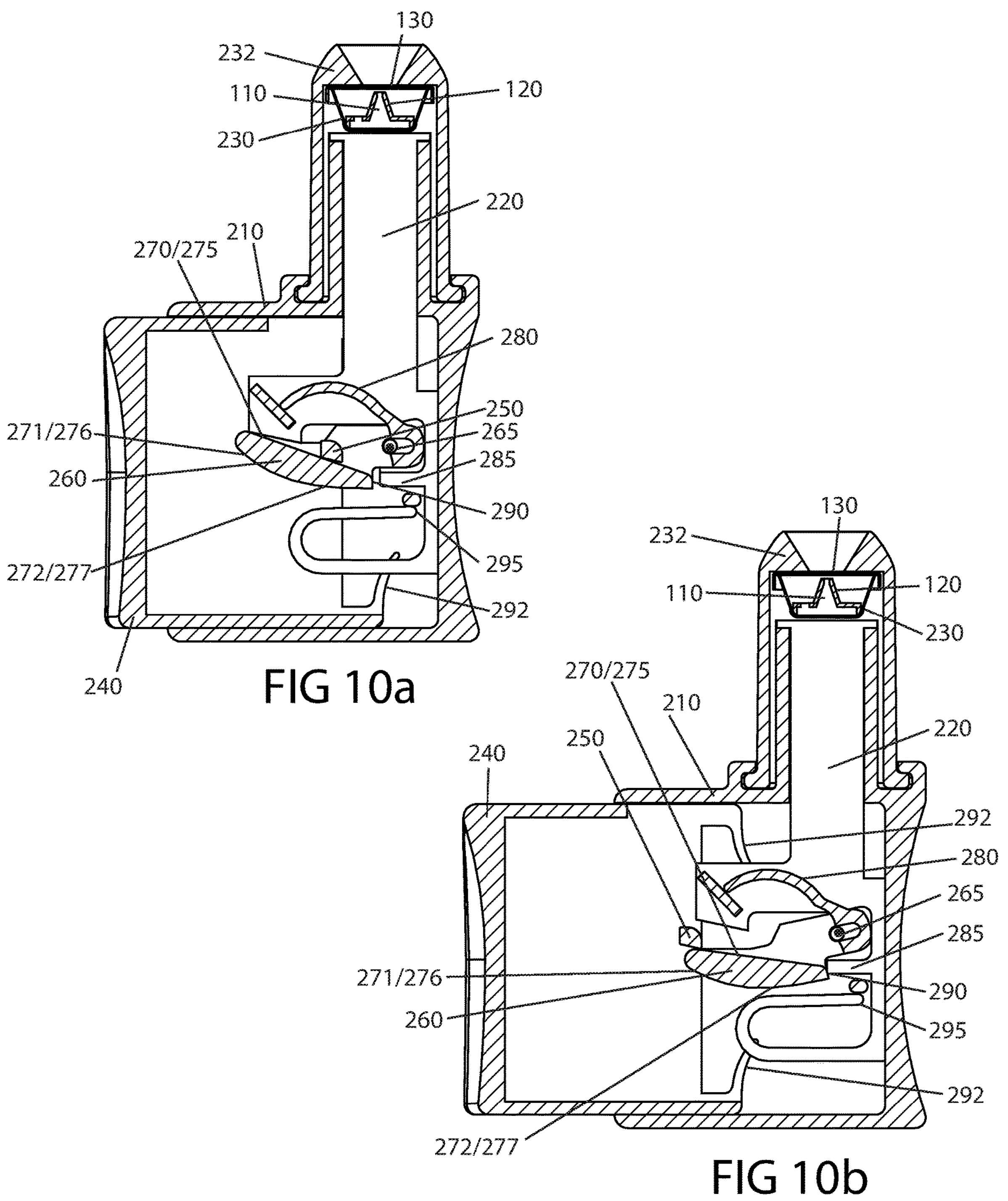
FIGS. 10A and B show an exemplary handheld assembly with an alternative escapement embodiment.

In yet other embodiments, plunger escapement member 260 may pivot at one or more different axes points as shown for example in FIGS. 10A and 10B. Here, axis 265 is located away from the main body of escapement 260 whereby a pin may translate within a slotted portion of the base of plunger escapement return spring 280. As shown in FIG. 10A, as dispense button 240 is withdrawn during the early portion of the make ready stage, drive member 250 moves along ramp surface 270 and escapement 260 pivots downward about axis 265 located to the rear (in the right in the figure) of the escapement. FIG. 10B depicts drive member 250 near the end of ramp 270 with escapement 260 rotated downward, dispense button 240 fully withdrawn and the assembly in a make ready state.

Figure 11:
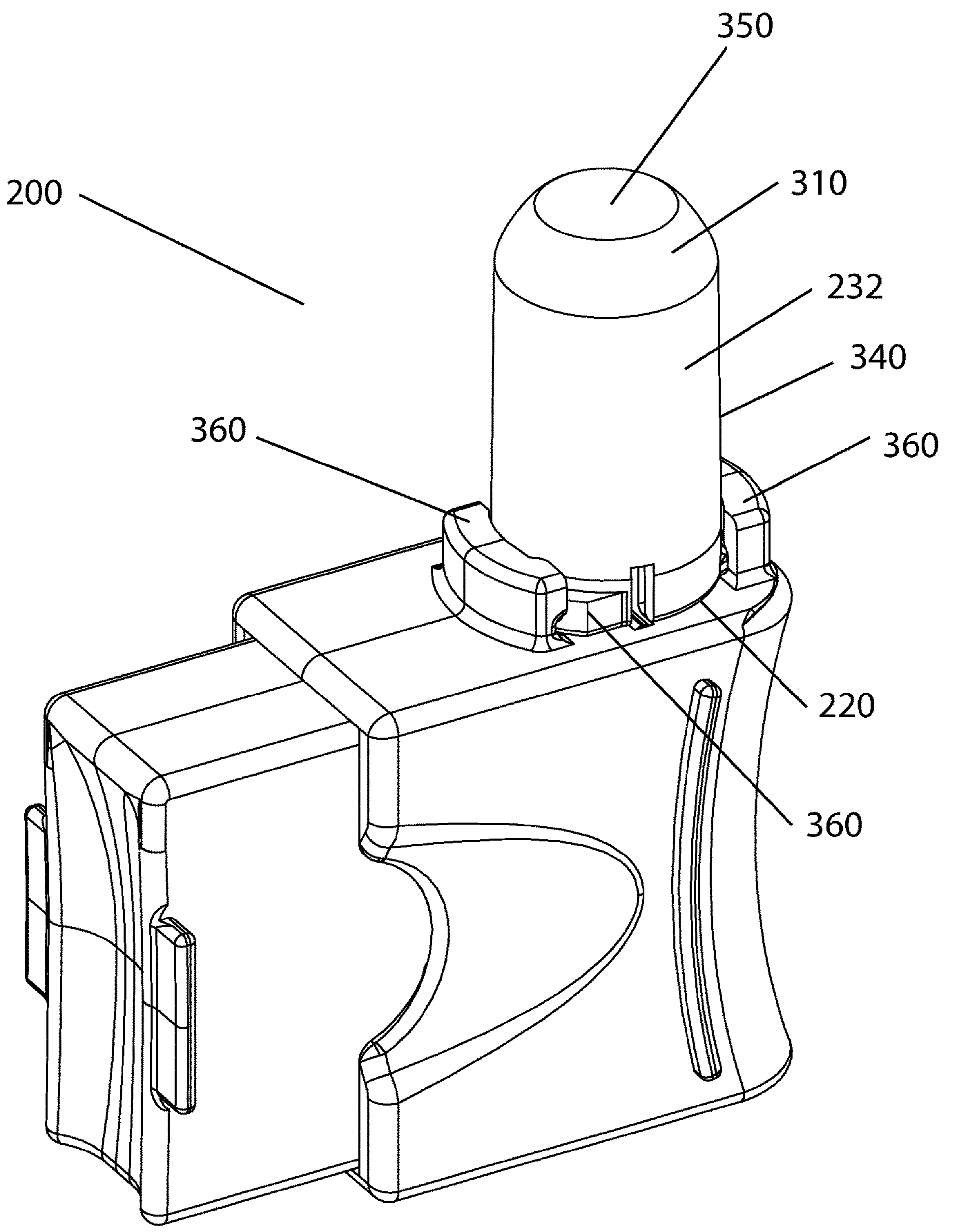
FIG. 11 shows an exemplary handheld assembly with an interlocking dispense tip.

In multi-use, reusable embodiments, assembly 200 may further comprise a removable dispense tip as shown in FIG. 11. Dispense tip 232 includes a unit dose form 230 (not shown) containing a medicament 235 (not shown) as in previous embodiments. In preferred embodiments, unit dose form 230 includes an internal piercing member 110 with an internal channel 120. The unit dose is preloaded in the distal end 310 of a dispense tip 232 which in this embodiment has a cylindrical hollow body 340 along its axis. The distal end 310 may be domed or other shape configured to receive and interact with unit dose 230 and has a thru hole 350 from which the medicament is dispensed to a subject.

One or more splines 360 may be located upon an upper surface of shell 210 and proximate and at least partially circumferential to the opening in shell 210 for plunger 220. Splines 360 may be semi-circular with a radius similar to that as the plunger 220 opening and are configured to rotatably interlock with one or more tabs 370 located at the lower end of body 320 of dispense tip 232. The tabs 370 and splines 360 thus provide for the ability to removably affix the dispense tip to the shell for reloadable operation.

Figure 12:
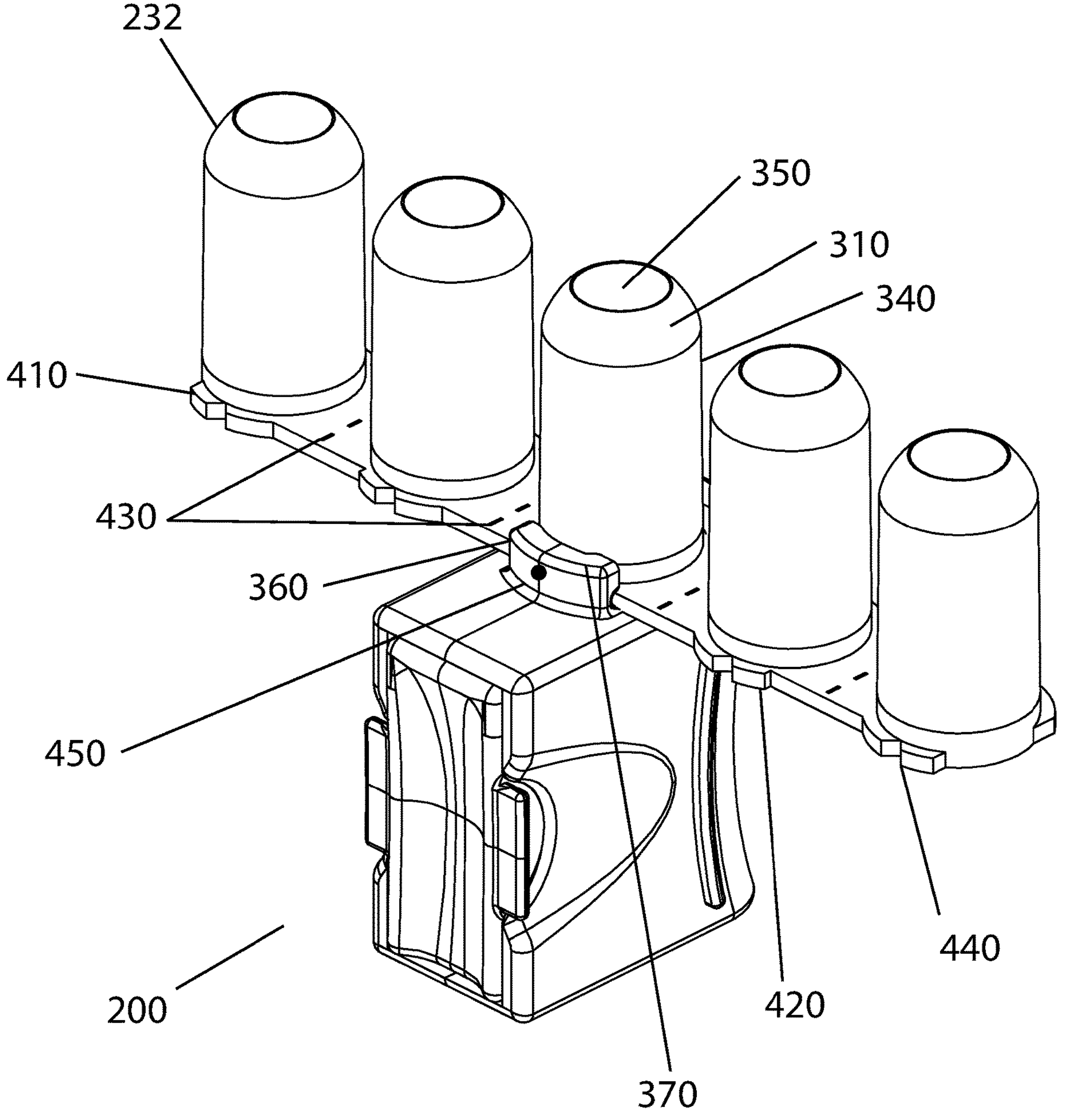
FIG. 12 shows an exemplary handheld assembly with a strip of interlocking dispense tips.

In yet other embodiments, for example as shown in FIG. 12, the dispense tip 232 may be configured in strips 410 comprising a linear array of more than one preloaded dispense tip 232. In this embodiment, dispense tip 232 tabs 370 are replaced by two oppositely located continuous lips 420 configured to slide though splines 360. The strip may be manually loaded and advanced by a user without additional mechanisms for simplicity and cost effectiveness. Lip(s) 420 may also include indentations 440 along their lengths which interact with protrusion points 450 within splines 360 to provide a click sensation as the strip is being advanced to indicate to the user the correct lateral position of next dispense tip.

Thus, in this embodiment with a reusable handheld dispensing assembly with a cycling plunger is provided with a loadable multi-dose array. Further, more than one dispense tip may thus be inexpensively molded together as a single unit and provided in a number to a user according to a particular dosing schedule. The strip 410 may also include separation points 430 in between individual dispense tips to facilitate separation of longer arrays into prescribed numbers, and/or detachment of dispensed doses by a user.

What is claimed is:

1. A handheld assembly for dispensing a medicament to a subject, the assembly comprising: a unit dose form containing the medicament; a shell configured for housing components of the handheld assembly; a plunger at least partially enclosed within the shell and extending from the shell and configured to express the unit dose form; a dispense button at least partially enclosed within the shell and extending from the shell and in slidable communication with the shell; a drive member located within the shell and in communication with the dispense button; a plunger escapement member rotatable about an axis within the shell and having more than one ramp wherein each ramp has a predetermined profile; wherein a first motion of the dispense button causes the drive member to translate along a first ramp of the plunger escapement member readying the assembly for dispense, and wherein a second motion of the dispense button causes the drive member to translate along a second ramp of the plunger escapement member extending the plunger to express the unit dose form, and wherein the unit dose form further comprises an internal piercing member located inside the unit dose form and configured to puncture a lidding material of the unit dose form from the inside upon the second motion of the dispense button.

2. The assembly of claim 1, wherein the drive member is comprised of a protruding body integral with or attached to the dispense button.

3. The assembly of claim 1 further comprising a plunger escapement member return spring disposed within the shell.

4. The assembly of claim 1, further comprising a dispense button return spring disposed within the shell.

5. The assembly of claim 1, wherein the number of plunger escapement member ramps is two and the first and second ramps are each disposed on different sides of the plunger escapement member.

6. The assembly of claim 1, wherein the plunger further comprises a planar hold surface disposed within the shell that maintains the plunger in a dispense state for a predetermined time at the end of dispense.

7. The assembly of claim 1, wherein the plunger escapement member further comprises at least three ramps of which one is configured as a reset ramp to return the assembly to an original static position.

8. The assembly of claim 1, wherein at least one of the ramps of the plunger escapement member has a predetermined profile with more than one discrete section.

9. The assembly of claim 1, wherein the internal piercing member further comprises an internal channel.

* * * * *